(12) United States Patent
Orfao De Matos Correia E Valle

(10) Patent No.: US 7,332,295 B2
(45) Date of Patent: Feb. 19, 2008

(54) MULTIDIMENSIONAL LEUKOCYTE DIFFERENTIAL ANALYSIS

(75) Inventor: Alberto Orfao De Matos Correia E Valle, Salamanca (ES)

(73) Assignee: Universidad de Salamanca, Salamanca (ES)

( * ) Notice: Subject to any disclaimer, the term of this patent is extended or adjusted under 35 U.S.C. 154(b) by 895 days.

(21) Appl. No.: 10/163,338

(22) Filed: Jun. 7, 2002

(65) Prior Publication Data

US 2003/0215892 A1 Nov. 20, 2003

(30) Foreign Application Priority Data

May 14, 2002 (EP) .................................... 2380098

(51) Int. Cl.
*G01N 33/00* (2006.01)
(52) U.S. Cl. .................. 435/7.24; 435/7.21; 435/7.23; 435/7.24; 435/40.5; 435/371.1; 435/371.2; 435/371.3; 436/522; 436/524; 436/528; 436/10; 436/17; 436/18; 436/56; 436/63; 436/64; 436/164; 436/172
(58) Field of Classification Search ............... 435/7.21, 435/7.23, 7.25, 40.5, 287.2, 287.3, 973, 7.24, 435/372.1, 372.2, 372.3; 436/519, 522, 10, 436/56, 63, 64, 165, 172, 175, 819, 16–18, 436/524, 528, 164; 422/68.1, 82.07, 73
See application file for complete search history.

(56) References Cited

U.S. PATENT DOCUMENTS

| | | | |
|---|---|---|---|
| 4,284,412 A | 8/1981 | Hansen et al. | |
| 4,520,110 A | 5/1985 | Stryer et al. | |
| 4,542,104 A | 9/1985 | Stryer et al. | |
| 4,727,020 A | 2/1988 | Recktenwald et al. | |
| 5,047,321 A | 9/1991 | Loken et al. | |
| 5,137,809 A | 8/1992 | Loken et al. | |
| 5,627,037 A | 5/1997 | Ward et al. | |
| 6,287,791 B1 | 9/2001 | Terstappen et al. | |
| 6,589,526 B2 * | 7/2003 | Crawford et al. | ........ 424/93.71 |
| 6,900,023 B1 * | 5/2005 | Houwen et al. | ........... 435/7.24 |

OTHER PUBLICATIONS

Braylan et al., Optimal Number of Reagents Required to Evaluate Hematolymphoid Neoplasias: Results of an International Consensus Meeting, Cytometry 46: 23-27 (2001).*
Bowen et al., Abnormal Patterns of Expression of CD16 and CD11b antigens by developing neutrophils in the bone marrow of patients with myelodysplastic syndrome, Laboratory Hamatology 3: 292-298 (1997).*

* cited by examiner

*Primary Examiner*—Gailene Rio Gabel
(74) *Attorney, Agent, or Firm*—Crowell & Moring LLP

(57) ABSTRACT

This invention relates to an improved procedure for the multiparameter analysis of leukocyte subpopulations from peripheral blood, bone marrow or any body fluid containing blood nucleated cells, including the quantification of each subpopulation in terms of cells per microliter. The method uses a cocktail of at least four monoclonal antibodies labelled each with a different fluorescent tag, the measurement of at least two light scatter and four fluorescence emissions related parameters and at least one population of fluorescent beads to differentiate and enumerate between and among the different leukocyte subpopulations in the peripheral blood, the bone marrow or other body fluid. It includes: the incubation of the sample with a mixture of monoclonal antibodies conjugated to a minimum of four different fluorochromes, the addition of one or more populations of reference beads, the flow cytometry measurement of the fluorescence emissions associated to each cell and bead population and, the mutidimesional analysis of each cell and bead population present in the sample aimed at its identification, enumeration and characterization.

17 Claims, 2 Drawing Sheets

Fig. 2

| GATE | LOGICAL DEFINITION | LEUCOCYTE/BEAD SUBSET |
|---|---|---|
| G1 | R4 | Counting reference beads |
| G2 | R1 or R2 or R3 | Total leukocytes |
| G3 | G2 and R5 and R8 and R10 | neutrophils |
| G4 | G2 and R6 and R9 and R11 | eosinophils |
| G5 | G2 and R7 and R12 | monocytes |
| G6 | G2 and R7 and R13 and R14 and not G3 and not G4 and not G5 | Basophils |
| G7 | G2 and R7 and R16 and not G3 and not G4 and not G5 and not G6 | Lymphocytes |
| G8 | G2 and R7 and R15 and not G3 and not G4 and not G5 and not G6 and not G7 | |
| G9 | G8 and R17 | Lymphoid dendritic cells |
| G10 | G8 and R18 | CD16+ dendritic cells/monocytes |
| G11 | G8 and R19 | Myeloid-dendritic cells |
| G12 | G9 or G10 or G11 | Total dendritic cells |

MULTIDIMENSIONAL LEUKOCYTE DIFFERENTIAL ANALYSIS

FIELD OF THE INVENTION

This invention relates to the field of flow cytometry and more particularly to the analysis of leukocyte cells from blood, bone marrow or any body fluids containing leukocytes. The invention enables the calculation of blood and bone marrow differentials of the leukocyte subpopulations in terms of both their relative frequencies by means of using multiparameter flow cytometry measurements of the cellular samples in combination with a reference bead suspension.

BACKGROUND OF THE INVENTION

In U.S. Pat. No. 5,047,321, Loken and Terstappen described the multiparameter analysis of cellular components in a body fluid. The body fluids described included blood and bone marrow. Using a combination of two nucleic acid dyes, a fluorescently labeled monoclonal antibody and two light scatter parameters, Loken and Terstappen were able to discriminate between and among various components of blood and bone marrow, count the number of cells within each component and provide a differential analysis of each. Using a combination of LDS-751 (Exciton) as a DNA dye, Thiazole Orange ('TO', Molecular Probes, Inc.) as an RNA dye, a fluorescently labelled anti-CD45 monoclonal antibody and forward and orthogonal light scatter on whole blood or bone marrow aspirates, Loken and Terstappen were able to detect and differentiate between erythrocytes, reticulocytes, nucleated erythrocytes, platelets, lymphocytes, monocytes, neutrophilic granulocytes, basophilic granulocytes, eosinophilic granulocytes and precursors of all nucleated cells but not other normal (i.e dendritic cells) or pathologic (leukemic blasts) leukocytes.

In U.S. Pat. No. 6,287,791, Terstappen and Chen described a further refinement of U.S. Pat. No. 5,047,321, but were not showing any better characterization of the different leukocyte subpopulations.

In U.S. Pat. No. 5,137,809, Loken and Sha described the multiparameter analysis of cellular components in bone marrow. The authors used a combination of monoclonal antibodies labeled with different fluorochromes to stain all leukocytes in a first step and then stain selected subpopulations in a second step.

All the methods referenced above were able to identify the majority of the leukocytes and were only identifying selected subpopulations as identified by the monoclonal antibodies used. Also, given the enumeration of the leukocyte subpopulations in terms of percentage of total leukocytes, it is impossible to link the obtained profile to the results as obtained by the traditional hematology cell counters. Under that condition, the different pathways identified remain isolated from the key diagnostic test that is in common use in all clinical laboratories.

In U.S. Pat. No. 5,627,037, Ward et al. describe a one-step method for the detection and the enumeration of absolute counts of one or more cell populations in a blood sample. The method employs a reagent comprising a mixture of one or more cell markers, a fluorescent microparticle and a fixative. The method refers to the absolute counting of leukocytes, such as CD4+ lymphocytes but does not give any indication of how to enumerate individual leukocyte subpopulations within this sample/reagent mixture.

SUMMARY OF THE INVENTION

The present invention comprises a method for the simultaneous, multi-parameter analysis of cells in a body fluid, such as blood and bone marrow among others. Such body fluids may derive from either normal or pathologic samples. For each cell present in a sample of cells taken from blood, bone marrow, or other body fluids, at least two measures of light scatter are taken and at least four measures of fluorescence are taken. The four fluorescence components comprise four different fluorochromes each linked to a different monoclonal antibody. Each antibody is capable of recognizing a different antigen expressed in different amounts on the various subpopulations of the leukocyte cells in the sample. Each fluorochrome's emission is distinguishable from the others.

The cells in the sample are mixed together with one or more populations of fluorescent microparticles and a mixture of monoclonal antibody reagents to which an erythrocyte lysing solution may be added. Subsequently, the sample is analyzed by means of a flow cytometer wherein the cells are passed one at the time through one or more sensing regions. In each of the sensing regions, the cells and beads are individually exposed to a source of light at a single wavelength and individual cellular measurements are recorded of at least two light scatter parameters and at least four fluorescence parameters for each cell and bead. The data recorded for each cell and bead are analyzed in real time or stored in a data storage and analysis facilities, such as a computer. U.S. Pat. No. 4,284,412 describes the configuration and the use of a typical flow cytometer equipped with a single light source and U.S. Pat. No. 4,727,020 describes the configuration and use of a flow cytometer equipped with two light sources.

In a preferred embodiment of this invention, the cell surface markers comprise monoclonal antibodies. The set of monoclonal antibodies chosen consists of a mixture of anti-HLA-Dr, anti-CD33, anti-CD45 and anti-CD14 to which an anti-CD38 reagent might be added as a fifth marker conjugated with a fifth fluorochrome. The CD number of the monoclonal antibodies is a cluster designation number assigned by the International Workshop and Conference on Human Leukocyte Differentiation Antigens and many examples of each antibody have been made commercially as well as independently and have been submitted to the Workshop for clustering.

The antibodies can be directly conjugated to a fluorescent label or can be indirectly labelled with, for example, a goat anti-mouse antibody conjugated directly to the fluorescent label; however, direct conjugation is preferred. Fluorescent labels that can be used in practice with this invention include fluorescein isothiocyanate (FITC), phycoerythrin (PE), peridinin chlorophyll protein (PerCP), allophycocyanin (APC), cyanin-5.5 (Cy5.5) and conjugates thereof coupled to PE or to PerCP (e.g. PE-Cy5, PerCP-Cy5.5, PE-Cyanin 7). The preferred combination of labels is FITC, PE, PerCP-Cy5.5 and APC. U.S. Pat. No. 4,520,110 describes the composition and the use of PE conjugated to a monoclonal antibody, and U.S. Pat. No. 4,542,104 describes the composition and use of PE in a paired conjugate format. U.S. Pat. No. 4,876,190 describes the composition and use of PerCP.

In a preferred method, a sample of a body fluid, such as blood or bone marrow, is taken and is mixed with the buffer containing a fluorescent microparticle in known numbers and a fluorescently labeled anti-HLA-Dr monoclonal antibody, a fluorescently labeled anti-CD33 monoclonal antibody, a fluorescently labeled anti-CD45 monoclonal antibody and a fluorescently labeled anti-CD14 monoclonal antibody (or only the aforementioned fluorescently labeled antibodies without microparticles). A fifth anti-CD38 monoclonal antibody reagent conjugated to a fifth fluorochrome might also be added. After gently mixing and incubation, an erythrocyte lysing solution may be added or alternatively the sample is directly run on a flow cytometer, such as a dual laser FACS Calibur™ brand flow cytometer (BD Biosciences) or a five-color flow cytometry instrument if a fifth flurochrome-conjugated anti-CD38 reagent was used. Cells are substantially analyzed one at a time and forward light scatter, orthogonal light scatter and four fluorescence emissions are separately measured and recorded for each cell. The six (or seven) parameters directly measured for each cell are then recorded in one or more combinations to identify and characterize each cell. Typically events classified to belong to a given cell population will be defined as those events that cluster in specific regions of the 6-dimensional (or 7-dimensional) space created as defined below. The method of this invention can be used to both identify all individual leukocyte subpopulations and enumerate each of these subpopulations in terms of concentration in the sample (number of cells per microliter of sample). For that purpose specific identification of the reference beads is needed to derive the absolute number of cells present in a given sample volume.

A more detailed explanation of the procedure for the analysis of the results obtained from the flow cytometric measurement of samples stained and prepared as described above, is described below in combination with the drawings enclosed.

BRIEF DESCRIPTION OF THE DRAWINGS

FIG. 2 comprises a set of cell selection gates in a logical sequence. The application of the cell gates in this sequence results in the systematic definition of a series of subpopulations of leukocytes and beads as depicted. The number of leukocytes subpopulations that can be selectively identified in peripheral blood samples from healthy volunteers with the help of the gate selection sequence, totals eight subpopulations. In addition, one gate is selected for the enumeration of the beads to assist in the calculation of the cell concentration for each subpopulation.

LEGENDS TO FIGURES

Figure 1:
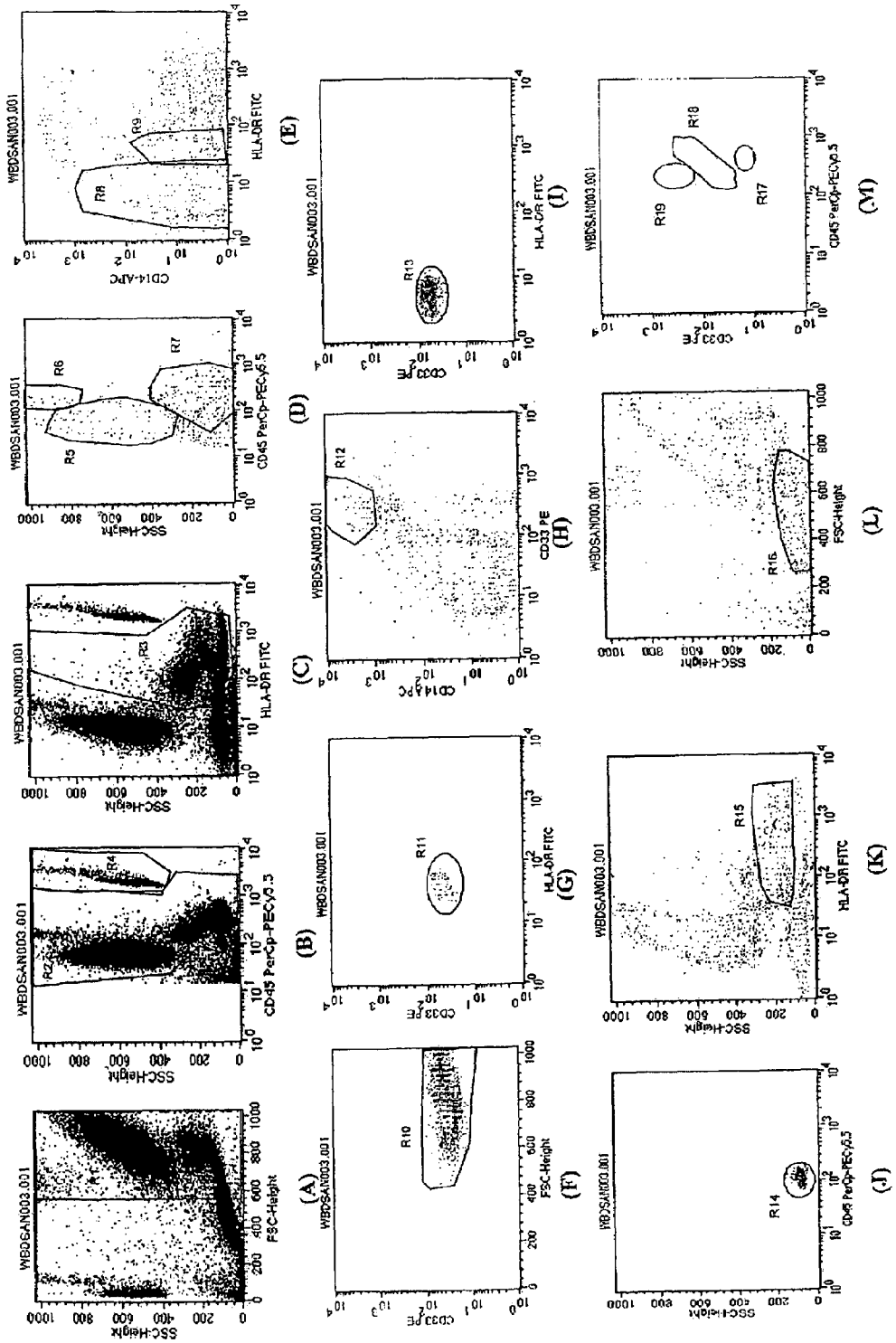
FIG. 1 comprises a series of thirteen dot plots of cells from lysed peripheral whole blood that have been labeled with anti-HLA-Dr-FITC, anti-CD33-PE, anti-CD45-PerCP-Cy5.5 and anti-CD14-APC wherein (A) is a bivariate plot of forward light scatter (FSC) versus orthogonal light scatter (SSC), (B) is a bivariate scattergram of SSC versus anti-CD45-PerCP-Cy5.5 fluorescence, (C) is a bivariate plot of orthogonal light scatter versus anti-HLA-Dr-FITC fluorescence, (D) is a gated bivariate plot of orthogonal light scatter versus anti-CD45-PerCP-Cy5.5 fluorescence, (E) is a gated bivariate plot of anti-CD14-APC fluorescence versus anti-HLA-Dr-FITC fluorescence, (F) is a gated bivariate plot of FSC versus anti-CD33-PE fluorescence, (G) is a bivariate scattergram of anti-HLADr-FITC versus anti-CD33-PE fluorescence, (H) is a bivariate plot of anti-CD14-APC fluorescence versus anti-CD33-PE fluorescence, (I) is a gated bivariate plot of anti-CD33-PE versus anti-HLA-Dr-FITC fluorescence, (J) is a gated bivariate plot of orthogonal light scatter versus anti-CD45-PerCP-Cy5.5 fluorescence, (K) is a gated bivariate plot of orthogonal light scatter versus anti-HLA-Dr-FITC fluorescence, (L) is a gated bivariate plot of orthogonal light scatter versus forward light scatter and (M) is a gated bivariate plot of anti-CD33-PE fluorescence versus anti-CD45-PerCP-Cy5.5 fluorescence.

FIG. 1.—Representative dot plots and regions used for the identification of the different cell subsets and beads measured by flow cytometry after staining a peripheral blood sample from an healthy volunteer with a combination of HLADR-FITC/CD33-PE/CD45-PerCPCy5.5/CD14-APC in a TrueCOUNT tube.

FIG. 2.—Logical gates described in the text and its relationship with both the regions illustrated in FIG. 1 and the specific subpopulation of leukocytes identified in a normal peripheral blood sample.

DETAILED DESCRIPTION OF THE INVENTION

Below the procedure described in this invention is illustrated by the following example which is not limiting the applicability and the scope of the invention:

EXAMPLE 1

Material and Methods

Normal whole blood was obtained from healthy volunteers after informed consent. For each test, 100 µL of whole blood from an EDTA Vacutainer tube (BD) was added to a bead product for absolute counting in cytometry such as a tube containing a known number of beads sold under the trade names TRUCOUNT (BD Biosciences), FLOWCOUNT (Beckmann/Coulter Hialeth, Fla.) or PERFECTCOUNT beads (Cytognos, Salamanca, Spain). To this sample tube, 5 µL of anti-HLA-Dr-FITC reagent, 5 µL of anti-CD33-PE reagent, 5 µL of anti-CD45-PerCP-Cy5.5 reagent and 5 µL of anti-CD14-APC reagent (BD Biosciences) were added and gently mixed for 5 seconds. This reagent/sample mixture was incubated for 15 minutes in the dark at room temperature. Subsequently 2 mL of FACS Lysing Solution (BD Biosciences), diluted 1:10 with distilled water, were added. This new reagent/sample mixture was gently mixed for 5 seconds and incubated for another 15 minutes in the dark at room temperature. The reagent/sample mixture was kept in the dark until they were run on a dual laser FACSCalibur brand flow cytometer. The stained cells should be analyzed within two hours following the addition of the FACS Lysing Solution. The sample data were recorded and analyzed on a G4 Macintosh computer equipped with CellQuest Pro software for a total of 60,000 events per sample. During acquisition information was recorded after thresholding for those events which showed positivity for CD45 and/or HLADR and/or had high forward light scatter (FSC) values, in order to restrict data acquisition to leukocytes and nucleated cells and to eliminate most of the events corresponding to non-nucleated red cells, platelets and debries.

In FIG. 1 the sequence used for data analysis is illustrated by up to thirteen different representative bivariate dot plots (or scattergrams), for a normal peripheral lysed whole blood sample. In dot plots (A), (B) and (C) all events acquired are displayed. In order to specifically select the nucleated cells and the beads present among all events regions were set as to include those events with intermediate/high FSC (region 1 in plot A) and/or positivity for CD45 (region 2 in plot B) and/or positivity for HLADr (region 3 in plot C), independently of their sideward light scatter values. R4 in plot B identifies the reference beads (gate 1, see below):

- Plot (A) is a scattergram of FSC versus orthogonal light scatter (SSC). All events acquired are shown and a region called out as region 1 or R1 is selected to identify the largest cells.
- Plot B is a bivariate histogram of SSC versus anti-CD45-PerCP-Cy5.5 fluorescence. All events acquired are shown and a gate, called out as region 2 or R2, is selected to separate the non-nucleated red cells, platelets and cell debris at the lower right end of the display from the leukocyte populations on the right hand side of the gate. R4 drawn in this dot plot identifies the bead population.
- Plot C is a scattergram of orthogonal light scatter (SSC) versus anti-HLA-Dr-FITC fluorescence. All events are shown and a third gate, called out as region 3 or R3, is selected to separate the large cluster of cells on the left hand side of the display together with some low scatter, low fluorescence expression from the cell populations on the lower right hand side of the display.

To proceed with the cell selection and enumeration, an electronic 'gate' (Gx) will be defined that can contain logical combinations of the identified regions under the logical functions 'AND', 'OR' and 'AND NOT'. If a gate defines a 'AND' function between regions, all events summed in the gate (Gx) will be events that belong to region Rx AND region Ry. If a gate defines a 'OR' function between regions, all events summed in the gate (Gx) will be events that belong to region Rx OR to region Ry. If a gate defines a 'AND NOT' function between regions, all events summed in the gate (Gx) will be events that belong to region Rx AND NOT to region Ry.

Gate 1 or G1 includes those events include in region 4 or R4 and corresponds to the counting beads.

A fourth scattergram (D) is generated, identical to (B), with orthogonal light scatter versus anti-CD45-PerCP-Cy5.5 fluorescence except for the fact that in this bivariate dot plot only those events corresponding to the nucleated cells—events included in gate 2 or G2=(not R4 AND R1 AND/OR R2 AND/OR R3)—are shown. Using these definitions, in a normal peripheral blood the nucleated cells will represent the total leukocyte concentration which in the sample can therefore be found under gate 2 (G2).

In this fourth bivariate dot plot three major distinct groups of events are identified called out as region 5 (or R5), region 6 (or R6) and region 7 (or R7). R5 defines the large middle population of events and R6 defines the population at the upper end of the scattergram containing events having very large orthogonal scatter values. R7 groups the events at the lower right end of the scattergram and bundles several clusters of events that will require further separation in the subsequent steps. By further using the 'Gate' tool as defined above, we can define specific leukocyte subsets which are included within these three regions: R5 to R7, both included.

Plot E shows a bivariate scattergram of anti-CD14-APC versus anti-HLA-Dr-FITC fluorescence for those events included in R5. Within this scattergram (plot E) two regions (R8 and R9) are defined: one (R8) to the left of the center of the scattergram and the other just to the right of R8 (R9), as shown in FIG. 1.

Plot F shows a FSC versus CD33-PE bivariate scattergram and plot G an HLADr-FITC versus CD33-PE dot plot histogram; in these plots (F and G) two regions (R10 and R11) are defined as depicted in FIG. 1: one (R10 in plot F) includes CD33-PE dim/intermediate positive events with intermediate to high FSC values while the other region (R11 in plot G) includes autofluorescent events which cluster as HLADr-FITC negative and CD33 dimly positive cells. Using the 'Gate' tool as defined above, we can define specific leukocyte subsets which are included within the following sets of three regions: neutrophils (G3=G2 AND R5 AND R8 AND R10) and eosinophils (G4=G2 AND R6 AND R9 AND R11).

Plot (H) shows a scattergram of anti-CD14-APC fluorescence versus anti-CD33-PE fluorescence. A region 12 (R12) can be defined to enclose the cell cluster to the top right close to the center of the scattergram. Define gate 5 (G5) as the logical combination of gate 2 AND region 7 AND region 12—G5=G2 AND R7 AND R12-. Gate 5—G5—defines the concentration of the monocytes.

Plot (I) shows a scattergram of anti-CD33-PE fluorescence versus anti-HLA-Dr-FITC fluorescence. Region 13 can be drawn to enclose the cluster of the cells to the middle of the left hand side of the scattergram (CD33-PE positive, HLADr-FITC negative).

Plot (J) shows a scattergram of orthogonal light scatter versus anti-CD45-PerCP-Cy5.5 fluorescence. Region 14 (R14) can be drawn here to enclose the cluster of events to the middle lower part of the display (low SSC and CD45 positive dim). Define gate 6 (G6) as the logical combination of gate 2 AND region 7 AND region13 AND region14 AND NOT region 12 AND NOT gate 3 AND NOT gate 4 AND NOT gate 5 (G6=G1 AND R7 AND R13 AND R14 AND NOT R12 AND NOT G3 AND NOT GATE 4). G6 defines the concentration of the basophils.

Plot (K) shows a scattergram of orthogonal light scatter versus anti-HLA-Dr-FITC fluorescence. Draw the region 15 (R15) to enclose the population of events along the top of the horizontally extended population with low SSC.

Plot (L) shows a scattergram of orthogonal light scatter (SSC) versus forward light scatter (FSC). Define region 16 (R16) to enclose the cluster of events along the X-axis with low orthogonal light scatter (SSC) values. Define gate 7 (G7) as the logical combination of gate 2 AND region 7 AND region 16 AND NOT gate 3 AND NOT gate 4 AND NOT gate 5 AND NOT gate 6 (G7=G2 AND R7 AND R16 AND NOT G3 AND NOT G4 AND NOT G5 AND NOT G6). Gate 7—G7—defines the concentration of lymphocytes.

Define gate 8 (G8) as the logical combination of gate 2 AND region 7 AND region 15 AND NOT gate 3 AND NOT gate 4 AND NOT gate 5 AND NOT gate 6 AND NOT gate 7 (G8=G2 AND R7 AND R15 AND NOT G3 AND NOT G4 AND NOT G5 AND NOT G6 AND NOT G7).

Plot (M) shows a scattergram of anti-CD33-PE versus anti-CD45-PerCP-Cy5.5 fluorescence only for those events included in gate 8 (G8). Draw region 17 (R17), region 18 (R18) and region 19 (R19). Define gate 9 (G9) as the logical combination of gate 8 AND region 17 (G9=G8 AND R17). This gate 9—G9—defines the concentration of the lymphoplasmacytoid dendritic cells. Define gate 10 (G10) as the logical combination of gate 8 (G8) AND region 18. Gate 10—G10—defines the concentration of the CD16+dendritic cells/monocytes. Define gate 11 (G11) as the logical combination of gate 8 (G8) AND region 19 (R19). Gate 11—G11—defines the concentration of CD33+hi myeloid dendritic cells.

Define gate 12 (G12) as those events falling in gate 9 (G9) OR gate 10 (G10) OR gate 11 (G11). Gate 12—G12—defines the total concentration of the dendritic cells.

As result of the different and sequential analysis steps, up to ten (including sub-segmentation of the dendritic cell population) leukocyte subpopulations can be defined and enumerated in a normal peripheral blood sample. Using the bead count under the defined reagent/sample mixture, a concentration parameter can be calculated in terms of cells per microliter. This expression of results will allow a direct correlation with the hematology counters installed routinely in the clinical laboratories.

The enumerated and defined subpopulations have very well defined positioning characteristics in the different scattergrams. This is due to their specific fluorescence intensity labeling with the help of the monoclonal antibodies used. The analysis of a series of samples of healthy volunteers shows that each of the identified leukocyte subpopulations can be characterized in terms of coordinate positions of their gravity center along the x- and the y-axis for each bivariate dot plot. In addition, each of the subpopulations identified has characteristic limits of spread of the population distribution (CV). Both of these parameters (gravity position, spread) are included in the identification of the subpopulations.

The specific spacing found between each of the above listed normal peripheral blood subpopulations in the 6-multidimensional space created with the measurement creates the necessary space for any abnormal cell populations to show as a separate and non regular leukocyte cell cluster. Specific diseases result in a specific fingerprint on the scattergram with cell clusters in the non regular cell spaces. Based on these non regular cell clusters, disease states can be diagnosed and monitored.

This can be achieved both in ex vivo obtained samples and in vitro manipulated cell samples obtained for any research, diagnostic and/or prognostic purposes.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

The invention claimed is:

1. A method for multiparameter identification, enumeration or characterization of cells in a sample, comprising:
   (a) obtaining a sample from an individual;
   (b) adding the sample to a container containing a pre-measured amount of counting particles;
   (c) adding to the sample a cocktail of fluorescently labeled monoclonal anti-HLADr, anti-CD33, anti-CD45 and anti-CD14 antibodies, wherein the fluorescent labels on the antibodies have peak emission spectra different from each other;
   (d) incubating the container to allow binding of the antibodies to the cells;
   (e) measuring fluorescence intensities and light scatter emissions of all cells bound to the fluorescently labeled monoclonal antibodies, and of the counting particles with an instrument capable of detecting and recording the intensities of at least four different fluorescence emissions, forward light scatter and sideward light scatter for each of the counting particles and for each of the bound cells in the sample;
   (f) storing measurement results as computer readable data for each counting particle and for each bound cell;
   (g) applying software algorithms which use logical combinations of gates to determine scattergram position and spread of total leukocytes, neutrophils, eosinophils, basophils, monocytes, lymphocytes, total dendritic cells, CD16-positive dendritic cells/monocytes, myeloid-derived dendritic cells and lymphoplasmacytoid dendritic cells, in addition to the counting particles, whereby each of the cell types is identified and quantitatively enumerated in terms of cells per unit of volume; and
   (f) applying software algorithms that use logical combinations of gates whereby clustering cell populations different from the normal leukocyte populations are identified.

2. The method of claim 1 wherein the sample is a body fluid.

3. The method according to claim 2, wherein the body fluid comprises peripheral blood.

4. The method according to claim 2, wherein the body fluid comprises cerebrospinal fluid.

5. The method according to claim 2, wherein the body fluid comprises urine.

6. The method of claim 1 wherein the sample comprises bone marrow.

7. The method according to claim 1, wherein the counting particles are fluorescent particles.

8. The method according to claim 1, wherein the software gating algorithm using logical gates first selects the total leukocytes, second the neutrophils, third the eosinophils, fourth the monocytes, fifth the basophils, sixth the lymphocytes, seventh the lymphoplasmacytoid dendritic cells, eighth the CD16+dendritic cells/monocytes, ninth the myeloid dendritic cells, tenth the total dendritic coils and eleventh any clustering cell population.

9. The method according to claim 1, further comprising adding to the sample a lysing solution to lyse erythrocytes present in the sample.

10. The method of claim 1, wherein the fluorescent labels are selected from the group consisting of phycoerythrin, fluorescein isothiocyanate, allophycocyanin, texas red, peridinin chlorophyll protein, cyanin-5, and cyanin-5.5, cyanin-7.

11. The method of claim 1, wherein the labels are selected from the group consisting of a conjugate coupled to fluorescein isothiocyanate, a conjugate coupled to phycoerythrin, a conjugate coupled to allophycocyanin, and a conjugate coupled to peridinin chlorophyll protein.

12. The method according to claim 1, wherein the monoclonal antibodies are conjugated directly to the fluorescent labels.

13. The method according to claim 1, wherein the anti-HLADr monoclonal antibody is labeled with fluorescein isothiocyanate, the anti-CD33 monoclonal antibody is labeled with phycoerythrin, the anti-CD45 monoclonal antibody is labeled with the peridinin chlorophyll protein/cyanin-5-5 fluorochrome tandem and the anti-CD14 monoclonal antibody is labeled with allophycocyanin.

14. A method for multiparameter identification, enumeration or characterization of cells in a sample, comprising:
   (a) obtaining a sample from an individual;
   (b) adding the sample to a container containing a pre-measured amount of counting particles;
   (c) adding to the sample a lysing solution to lyse erythrocytes present in the sample;
   (d) adding to the sample a cocktail of fluorescently labeled monoclonal anti-HLADr, anti-CD33, anti-CD45 and anti-CD14 antibodies, wherein the fluorescent labels on the antibodies have peak emission spectra different from each other;

(e) incubating the container to allow binding of the antibodies to the cells;

(f) measuring fluorescence intensities and light scatter emissions of all cells bound to the fluorescently labeled monoclonal antibodies, and of the counting particles with an instrument capable of detecting and recording the intensities of at least four different fluorescence emissions, forward light scatter and sideward light scatter for each of the counting particles and for each of the bound cells in the sample;

(g) storing measurement results as computer readable data for each counting particle and for each bound cell;

(h) applying software algorithms which use logical combinations of gates to determine scattergram position and spread of total leukocytes, neutrophils, eosinophils, basophils, monocytes, lymphocytes, total dendritic cells, CD16-positive dendritic cells/monocytes, myeloid-derived dendritic cells and lymphoplasmacytoid dendritic cells, in addition to the counting particles, whereby each of the cell types is identified and quantitatively enumerated in terms of cells per unit of volume; and (i) applying software algorithms that use logical combinations of gates whereby clustering cell populations different from the normal leukocyte populations are identified.

15. The method according to claim 14, wherein the labels are selected from the group consisting of phycoerythrin, fluorescein isothiocyanate, allophycocyanin, texas red, peridinin chlorophyll protein, cyanin-5, cyanin-5.5, and cyanin-7.

16. The method according to claim 14, wherein the labels are selected from the group consisting of a conjugate coupled to fluorescein isothiocyanate, a conjugate coupled to phycoerythrin, a conjugate coupled to allophycocyanin and a conjugate coupled to peridinin.

17. The method according to claim 14, wherein the anti-HLADr monoclonal antibody is labeled with fluorescein isothiocyanate, the anti-CD33 monoclonal antibody is labeled with phycoerythrin, the anti-CD45 monoclonal antibody is labeled with the peridinin chlorophyll protein/ cyanin-5-5 fluorochrome tandem, and the anti-CD14 monoclonal antibody is labeled with allophycocyanin.

* * * * *